(12) United States Patent
Fehr et al.

(10) Patent No.: US 8,119,826 B2
(45) Date of Patent: *Feb. 21, 2012

(54) PROCESS FOR THE PREPARATION OF BETA-SANTALOL AND DERIVATIVES THEREOF

(75) Inventors: Charles Fehr, Versoix (CH); Magali Vuagnoux, Saint-Paul-en-Chablais (FR)

(73) Assignee: Firmenich SA, Geneva (CH)

( * ) Notice: Subject to any disclaimer, the term of this patent is extended or adjusted under 35 U.S.C. 154(b) by 70 days.

This patent is subject to a terminal disclaimer.

(21) Appl. No.: 13/012,567

(22) Filed: Jan. 24, 2011

(65) Prior Publication Data

US 2011/0118497 A1 May 19, 2011

Related U.S. Application Data

(63) Continuation of application No. 12/936,325, filed as application No. PCT/IB2009/052048 on May 18, 2009, now Pat. No. 7,902,393.

(30) Foreign Application Priority Data

May 20, 2008 (EP) ..................................... 08104028

(51) Int. Cl.
C07F 7/04 (2006.01)
C07C 69/74 (2006.01)
C07C 41/00 (2006.01)

(52) U.S. Cl. ......................... 556/445; 560/128; 568/671

(58) Field of Classification Search .................. 560/128; 568/671; 556/445
See application file for complete search history.

(56) References Cited

U.S. PATENT DOCUMENTS

| 2007/0053860 A1 | 3/2007 | Eh et al. ........................ 424/70.2 |
| 2010/0099904 A1 | 4/2010 | Dupau et al. .................... 556/136 |

FOREIGN PATENT DOCUMENTS

| EP | 0 010 213 A2 | 4/1980 |
| WO | WO 03/002491 A2 | 1/2003 |
| WO | WO 2005/037243 A1 | 4/2005 |
| WO | WO 2008/120175 A1 | 10/2008 |

OTHER PUBLICATIONS

International Search Report and Written Opinion of the International Searching Authority, Application No. PCT/IB2009/052048, Sep. 2, 2009.

Ahrendt et al., "New Strategies for Organic Catalysis: The First Highly Enantioselective Organocatalytic Diels—Alder Reaction," J. Am. Chem. Soc., 122:4243-4244 (2000).
Brunke et al., "The Chemistry of Sandalwood Odour—A Review of the Last 10 Years," Rivista Ital. EPOS, pp. 49-83 (1997).
Degny et al., "Déshydratation en phase liquide d'alcools bicycliques primaries," Bulletin de la Société Chimique de France, No. 12, pp. 4770-4777 (1972).
Gotoh et al., "Diarylprolinol Silyl Ether as Catalyst of an exo-Selective, Enantioselective Diels—Alder Reaction," Organic Letters, 9(15):2859-2862 (2007).
Hayashi et al., "Asymmetric Diels—Alder Reactions of α,β-Unsaturated Aldehydes Catalyzed by a Diarylprolinol Silyl Ether Salt in the Presence of Water," Angew. Chem. Int. Ed., 47:6634-6637 (2008).
Joachimsmann-Dufresne et al., "Réarrangements d'ions carbonium dans la série de l'isosanténe (Méthylène-2 méthyl-3 bicyclo(2.2.1)heptane)," Bulletin de la Société Chimique de France, No. 1, pp. 385-390 (1968).
Kretschmar et al., "The Total Synthesis and Geometric Configuration of dl-β-Santalol," Tetrahedron Letters, 1:41-44 (1970).
Krotz et al., "Total Syntheses of Sandalwood Fragrances: (Z)- and (E)-β-Santalol and Their Enantiomers, ent-β-Santalene," Tetrahedron: Asymmetry, 1(8):537-540 (1990).
Seebach et al., "On the Ti-TADDOLate-Catalyzed Diels—Alder Addition of 3-Butenoyl-1,3-oxazolindin-2-one to Cyclopentadiene. General Features of Ti-BINOLate- and Ti-TADDOLate-Mediated Reactions," J. Org. Chem., 60:1788-1799 (1995).
Simmons et al., "Aldehyde Enol Esters as Novel Chain Terminators in Cationic Olefin Cyclizations," Helvetica Chimica Acta, 71:1000-1004 (1988).
Snowden et al., "Stereoselective Syntheses of (±)-epi-β-Santalene and (±)-epi-β-Santalol," Helvetica Chimica Acta, 64(1):25-32 (1981).
Takahashi et al., "A New Method for the Introduction of Carbon-Carbon Triple Bond at C-13 in PG Synthesis. A Stereocontrolled Synthesis of ZK 96 480," J. Org. Chem., 53:1227-1231 (1988).
Wilson et al., "Enantioselective Organocatalytic Intramolecular Diels—Alder Reactions. The Asymmetric Synthesis of Solanapyrone D," J. Am. Chem. Soc., 127:11616-11617 (2005).

*Primary Examiner* — Jafar Parsa

(74) *Attorney, Agent, or Firm* — Winston & Strawn LLP

(57) ABSTRACT

The present invention relates to a dienol compound of formula

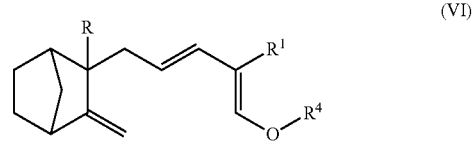

(VI)

in the form of any one of its stereoisomers or mixture thereof, wherein R represents a methyl or ethyl group; $R^1$ represents a hydrogen atom or a methyl or ethyl group; $R^4$ represents a $C_1$-$C_3$ alkyl, alkenyl or acyl group or a $C_3$-$C_8$ silyl group.

10 Claims, No Drawings

PROCESS FOR THE PREPARATION OF BETA-SANTALOL AND DERIVATIVES THEREOF

CROSS-REFERENCE TO RELATED APPLICATIONS

This application is a continuation of application Ser. No. 12/936,325 filed Oct. 4, 2010, now U.S. Pat. No. 7,902,393, which is the 371 filing of International Patent Application PCT/IB2009/052048, filed May 18, 2009.

TECHNICAL FIELD

The present invention relates to the field of organic synthesis and more specifically it concerns a process for the preparation of a compound of formula

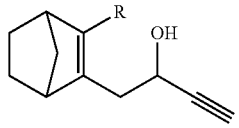

(I)

wherein R represents a Me or Et group, and said compound is in the form of any one of its stereoisomers or mixture thereof The invention concerns also the compound (I) as well as its precursors and the process to manufacturing compound (I). Furthermore, it concerns also the use of compound (I) for the synthesis of β-santalol or of derivatives thereof.

PRIOR ART

The compounds of formula (I) are novel compounds, and are useful starting materials for the preparation of β-santalol, and derivatives thereof, in a short and effective manner.

The β-santalol, and derivatives thereof, are well known perfuming ingredients, some of which of particular relevance. Therefore, there is always a need for alternative synthesis to produce them.

To the best of our knowledge, all known syntheses are very long or require expensive starting materials or reagents or even steps which are too expensive for an industrial process (e.g. see Brunke at al., in Rivista Italiana EPPOS, 1997, 49). In particular one may cite the following references, which are representative of the best examples of processes for the preparation of β-santalol:

EP 10213: however said process, besides the fact that it is very long, requires many chlorinated intermediates (not optimal for a use in perfumery) and provides a very low yield (about 13%) for the preparation of the unsaturated aldehyde (II) of the present invention (see below);

A. Krotz et all, in Tet. Asym, 1990, 1, 537: relatively short synthesis, however it requires two Wittig reactions, or the equivalent, and expensive reagents.

The aim of the present invention is to provide a more industrial process for the preparation of β-santalol, and derivatives thereof. Indeed the present invention shortens the overall process of preparation of the targeted compounds by allowing the one-step creation of a suitably functionalised side-chain moiety (with the correct configuration) together with the concomitant formation of the methylene function (without the mandatory need of a Wittig olefination).

DESCRIPTION OF THE INVENTION

The present invention relates to a compound of formula

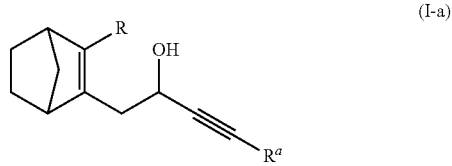

(I-a)

in the form of any one of its stereoisomers or mixture thereof, and wherein R represents a Me or Et group, and $R^a$ represents a hydrogen atom or a $Si(R^b)_3$ or $(R^c)_2COH$ group, $R^b$ representing $C_{1-5}$ group or a phenyl group and $R^c$ representing a $C_{1-5}$ group or a phenyl group.

Indeed, we have now found that β-santalol (an important perfuming ingredient), and derivatives thereof, can be advantageously prepared starting from an enynol of formula (I-a) wherein $R^a$ is a hydrogen atom, i.e. a compound of formula

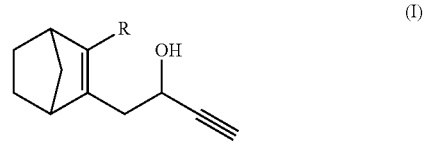

(I)

in the form of any one of its stereoisomers or mixture thereof, and wherein R represents a Me or Et group.

In particular, a compound (I) or (I-a) wherein R is Me is the preferred embodiment, since it is a direct precursor of β-santalol.

Compound (I) can be advantageously prepared from the compounds (I-a) wherein $R^a$ is not a hydrogen atom. Consequently, a second object of the present invention concerns a process for the preparation of a compound (I), as defined above, comprising the following steps:

a) reacting 2-R-3-methylene-bicyclo[2.2.1]heptane, wherein R has the same meaning as for compound (I), with a compound of formula $R^a$—C≡CCHO, wherein $R^a$ represents a $Si(R^b)_3$ or $(R^c)_2COH$ group, $R^b$ and $R^c$ representing, independently from each other, $C_{1-5}$ group or a phenyl group, in the presence of a Al, B or Sn derivative Lewis acid as catalyst ("ene" reaction),
to obtain a compound of formula (I-a) wherein $R^a$ represents a $Si(R^b)_3$ or $(R^c)_2COH$ group, $R^b$ and $R^c$ representing, independently from each other, $C_{1-5}$ group or a phenyl group; and b) treating the obtained compound (I-a) with a suitable base or a fluorine salt to obtain compound (I).

According to a particular embodiment, the starting material of the above process is 2endo-methyl-3-methylene-bicyclo[2.2.1]heptane, in an optically active or racemic form.

The catalysts necessary for an "ene reaction" are well known by a person skilled in the art, however one may cite, as non limiting examples, the following compounds: $Me_2AlCl$, $EtAlCl_2$, $SnCl_4$ or $BF_3$.

The bases of fluorine salt necessary for step b) are well known by a person skilled in the art, however one may cite, as non limiting examples, the following compounds: KOH, borax ($Na_2B_4O_7$) or KF.

The compound 2-R-3-methylene-bicyclo[2.2.1]heptane, racemic or in an optically active form and wherein R has the same meaning provided above, can be obtained according to the methods described in the prior art, or more conveniently according to a new process, which is also an object of the invention, comprising the following steps:

a') reacting cyclopentadiene with a trans aldehyde RHC=CHCHO, wherein R has the same meaning as above, under Diels Alder conditions, in the presence of an optically active salt obtained by:
  reacting together an acid H(Anion) and
  a racemic or optically active 2-$R^d$-3-$R^e$-5-$R^f$-4-imidazolidinone derivative or a racemic or optically active prolinol derivative of formula $(C_4H_8N)$-2-$CAr_2OSiR^b{}_3$;
  wherein Anions stand for an anion selected in the group consisting of Cl$^-$, ClO$_4{}^-$, a $R^gSO_3{}^-$ or $R^gCO_2{}^-$, wherein $R^g$ is a $C_1$-$C_7$ hydrocarbon group or an $C_1$-$C_8$ fluoroalkyl or fluoroaryl group, ClSO$_3{}^-$, FSO$_3{}^-$, BF$_4{}^-$, PF$_6{}^-$, SbCl$_6{}^-$, AsCl$_6{}^-$, SbF$_6{}^-$, AsF$_6{}^-$ or B($R^h$)$_4{}^-$, wherein $R^h$ is a phenyl group optionally substituted by one to five groups such as halide atoms or methyl or CF$_3$ groups;
  $R^b$ is defined as for compound (I-a); Ar represents a phenyl group optionally substituted by one, two or three Me, Et CF$_3$, OMe or OEt;
  $R^d$ represents t-Bu, a phenyl group, a benzyl group or a 5-Me-furyl group;
  $R^e$ represents a hydrogen atom, a $C_1$-$C_3$ alkyl group or a benzyl group; and
  $R^f$ represents t-Bu, a phenyl group, a benzyl group;
  (to obtain 3-R-bicyclo[2.2.1]hept-5-ene-2exo-carbaldehyde);

b') reducing the Diels Alder adduct obtained in step a') into a saturated alcohol, and optionally converting said alcohol into an ester, carbonate or a sulfonate;

c') converting said alcohol, ester, carbonate or sulphonate, into the desired product.

Step a') is a known reaction and a person skilled in the art is able to apply its standard knowledge to perform them (e.g. see MacMillan et al. in WO 03/002491 or in *J. Am. Chem. Soc.* 2005, 127, 11616 or see Hayashi et al. in *Angew. Chem. Int. ed.* 2008, 47, 6634 or in *Org. Lett.,* 2007, 9, 2859). Examples of how performing said process is provided in the Example part of the description.

Steps b') and c') are well known reactions and a person skilled in the art is able to apply its standard knowledge to perform them. Examples of how performing said process is provided in the Example part of the description.

For the sake of clarity, by "ester, carbonate or sulfonate" it is meant the usual meaning in the art, i.e. that the oxygen atom of said saturated alcohol is bonded to an acyl, alkoxycarbonyl or sulfonate group (e.g. a $C_{1-7}$ group).

Preferably R is a methyl group, and the aldehyde RHC=CHCHO is crotonaldehyde (i.e. the product obtained by said process, i.e. of steps a') and b') and c'), is 2-Me-3-methylene-bicyclo[2.2.1]heptane).

This process is particularly useful for the preparation of 2endo-R-3-methylene-bicyclo[2.2.1]heptane, in an optically active or racemic form, and subsequently a compound of formula (I-a').

As mentioned above, enynol (I) has been found to be a useful precursor of β-santalol, and derivatives thereof. Indeed enynol (I) can be used for the preparation of an aldehyde (II), as defined below, which is known to be an important intermediate in the preparation of β-santalol and derivatives thereof.

Consequently, the present invention also relates to a process for the preparation of a compound of formula

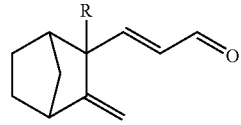

(II)

in the form of any one of its stereoisomers or mixture thereof, and wherein R represents a Me or Et group;
by reacting (cyclisation-fragmentation step) an enynol of formula

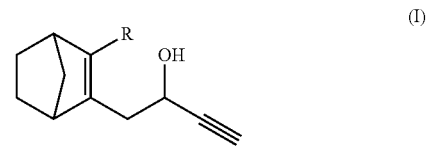

(I)

as defined above;
with a M(L)$_n$Z salt, wherein M represents Zn(II), Cu(I) or Ag(I), n represents an integer from 0 to 4, L represents a $C_1$-$C_4$ nitrile, $C_6H_5$CN, or di-nitrile, or a $C_5$-$C_8$ pyridine derivative, and Z a weakly or non coordinating anion.

According to a particular embodiment, said M(L)$_n$Z salt is Cu(L)$_4$Z, wherein L is $C_1$-$C_4$ nitrile, or a AgZ salt.

According to a particular embodiment Z is a $R^4SO_3{}^-$, wherein $R^4$ is a chlorine or fluorine atom or an $C_1$-$C_8$ alkyl, fluoroalkyl or fluoroaryl group, B$_4{}^-$, PF$_6{}^-$, SbCl$_6{}^-$, SbF$_6{}^-$, or BR$^5{}_4{}^-$, wherein $R^5$ is a phenyl group optionally substituted by one to five groups such as halide atoms or methyl or CF$_3$ groups. When M is Ag(I) then Z may also represent a nitrate or a perchlorate.

According to a preferred embodiment of the invention, Z is BF$_4{}^-$, PF$_6{}^-$, SbCl$_6{}^-$, C$_6$F$_5$SO$_3{}^-$, BPh$_4{}^-$, CF$_3$SO$_3{}^-$ or yet B[3,5-(CF$_3$)$_2$C$_6$H$_4$]$_4$−, more preferably BF$_4$−.

Optionally, to said process of the invention, it can be also added, as additive, an alkaline salt of the anion Z. In particular it can be added a salt of formula KZ or CsZ.

The transformation of (I) into (II), in any of its embodiments, is preferably carried out in the presence of solvent. Non-limiting examples of such a solvent are esters, aromatic hydrocarbons, chlorinated solvents and mixtures thereof. More preferably, the solvent is toluene or 1,2-dichloroethane and mixtures thereof.

The temperature, at which the transformation of (I) into (II) according to the invention can be carried out, in any of its embodiments, is comprised between 0° C. and 150° C., preferably between 40° C. and 70° C. Of course a person skilled in the art is also able to select the preferred temperature as a function of the melting and boiling point of the starting and final products and/or an eventual solvent.

The salt M(L)$_n$Z can be added to the reaction medium in a large range of concentrations. As non-limiting examples, one can cite salt concentrations ranging from 0.01 to 0.50 molar equivalents, relative to the molar amount of the starting enynol (I). Preferably, the salt concentration will be comprised between 0.01 and 0.10 molar equivalents. It goes without saying that the optimum concentration of the M(L)$_n$Z will depend on the nature of the latter and on the desired reaction time.

The additive can be added to the reaction medium in a large range of concentrations. As non-limiting examples, one can cite additive concentrations ranging from 10 to 250%, relative to the weight of the salt. Preferably, the additive concentration will be comprised between 10 and 120%, relative to the weight of the salt.

According to any embodiment of the invention, and independently of the specific aspects, the compounds (I-a), (I) or (II) can be in the form of any one of its stereoisomers or mixture thereof. By the term stereoisomer it is intended any diastereomer, enantiomer, racemate or carbon-carbon isomer of configuration E or Z.

According to a particular embodiment of the invention, compound (I-a) is in the form of a mixture of stereoisomers comprising more than 50% (w/w) of the (1R,4S) stereoisomer, i.e. a compound having the absolute configuration as shown in formula (I-a')

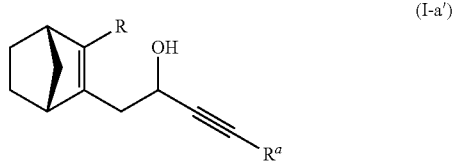

(I-a')

and in a further embodiment said compound (I) consists essentially in the compound (I-a').

According to a particular embodiment of the invention, compound (I) is in the form of a mixture of stereoisomers comprising more than 50% (w/w) of the (1R,4S) stereoisomer, i.e. a compound having the absolute configuration as shown in formula (I')

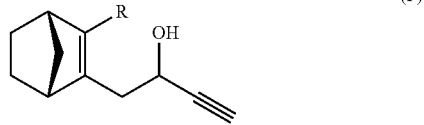

(I')

and in a further embodiment said compound (I) consists essentially in the compound (I').

As typical examples of compounds (I) one may cite 1-[-3-methylbicyclo[2.2.1]hept-2-en-2-yl]-3-butyn-2-ol or its stereoisomer 1-[(1R,4S)-3-methylbicyclo[2.2.1]hept-2-en-2-yl]-3-butyn-2-ol.

According to a particular embodiment of the invention, compound (II) is in the form of a mixture of isomers comprising more than 50% (w/w) of the 2-endo-R configuration. Furthermore, said compound (II) can be in the form of a mixture of stereoisomers comprising more than 50% (w/w) of the (1S,2S,4R) stereoisomer, i.e. a compound having the absolute configuration as shown in formula (II')

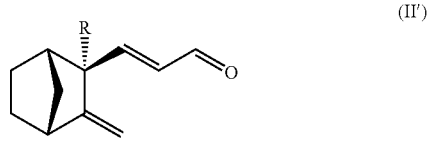

(II')

and in a further embodiment said compound (II) consists essentially in the compound (II').

As typical examples of compounds (II) one may cite 3-[2-methyl-3-methylenebicyclo[2.2.1]hept-2-yl]-acrylaldehyde or its stereoisomer 3-[(1S,2S,4R)-2-methyl-3-methylenebicyclo[2.2.1]hept-2-yl]-acrylaldehyde.

Since compound (I) is a useful starting material for the preparation of β-santalol or a derivative thereof, the present invention concerns also the use of a compound (I), as intermediate, in the synthesis of a compound of formula (III) as defined herein below. In other words, the invention concerns also a process for obtaining a compound of formula (β-santalol or derivatives)

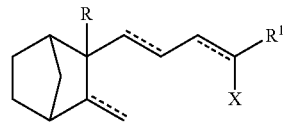

(III)

wherein R represents a Me or Et group;

R$^1$ represents a hydrogen atom or a Me or Et group;

X represents a $CH_2OR^2$, CHO or a $CH(OR^3)_2$ group, $R^2$ representing a hydrogen atom, a $C_1$-$C_3$ alkyl, alkenyl or acyl group, $R^3$ representing, when taken separately, a $C_1$-$C_3$ alkyl, alkenyl or acyl group or, when taken together, a $C_2$-$C_5$ alkanediyl group; and the dotted lines represents a single or double bond, said compound being in the form of any one of its stereoisomers or mixture thereof;

said process comprising the following steps:

1) transforming an enynol of formula (I), as defined above, into an aldehyde of formula (II), as defined above, by a process as described above; and 2) transforming the aldehyde of formula (II), into a compound of formula (III), as defined above.

According to a particular embodiment of the invention, and independently of the specific aspects, R represents a methyl group.

According to a further embodiment of the invention, and independently of the specific aspects, R$^1$ represents a methyl or ethyl group.

According to a further embodiment of the invention, and independently of the specific aspects, R$^2$ represents a hydrogen atom or a $C_1$-$C_3$ acyl group.

According to a further embodiment of the invention, and independently of the specific aspects, R$^3$ represents, when taken separately, a methyl or ethyl group or, when taken together, a $C_2$-$C_4$ alkanediyl group.

According to a particular embodiment of the invention, and independently of the specific aspects, the compounds (III) can be in the form of any one of its stereoisomers or mixture thereof. By the term stereoisomer it is intended any diastereomer, enantiomer, racemate or carbon-carbon isomer of configuration E or Z.

According to a particular embodiment of the invention, compound (III) is in the form of a mixture of isomers comprising more than 50% (w/w) of the 2-endo-R configuration. Furthermore, said compound (III) can be in the form of a mixture of stereoisomers comprising more than 50% (w/w) of the (1S,2S,4R), or even (2Z,1S,2S,4R), stereoisomer, i.e. a compound having the absolute configuration as shown in formula (III')

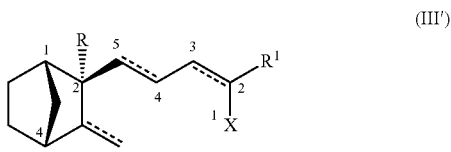
(III')

and in a further embodiment said compound (III) consists essentially in the compound (III').

As typical examples of compounds (III) one may cite the following: β-santalol, (−)-β-santalol (i.e (2Z)-2-methyl-5-[1S,2R,4R)-2-methyl-3-methylenebicyclo[2.2.1]hept-2-yl]-2-penten-1-ol), β-santalal, β-santalyl benzoate, β-santalyl butyrate, β-santalyl formate, β-santalyl proprionate.

The first step of the process is as defined above.

The transformation of the aldehyde (II) into the compound (III) can be performed in many different manners, which are well known by a person skilled in the art. Practical examples are provided in Examples herein below.

However, as non-limiting example, one of the most direct manners to transform the aldehyde (II) into the compound (III) comprises the following reactions:

i) coupling of aldehyde (II) with $Ph_3P=CHR^1$ and then reacting the glide with $CH_2O$ and BuLi (Wittig addition followed by a hydroxyalkylation) to obtain an alcohol or a carboxylate derivative;
ii) transformation of the alcohol into the suitable ester, aldehyde or acetal.

An optional step of partial or total hydrogenation of the C=C bonds can be perfomed at any moment, i.e. before step i), or just after step i) or ii).

The Wittig-hydroxyalkylation addition can be performed according to the method reported by R. Snowden et al. in Helvetica Chemica Acta, 1981, 64, 25.

The Wittig addition allows obtaining directly compound (III) where X represents $CH_2OR^2$, wherein $R^2$ is a hydrogen atom or some acyl groups. If a compound (III) with a different meaning of $R^2$ is desired, then said compound can be obtained by converting the alcohol (III) (X being $CH_2OH$) with any standard method as well known by a person skilled in the art. For example, an aldehyde of formula (III) can be obtained by oxidation of the alcohol (III), or an ester (III) can be obtained by esterification of said alcohol (III), etc.

Alternatively, the aldehyde (II) can be converted into the compound (III'), see below, by performing the following reactions:

a) reducing (hydrogenation) the aldehyde (II) into and aldehyde of formula (IV)

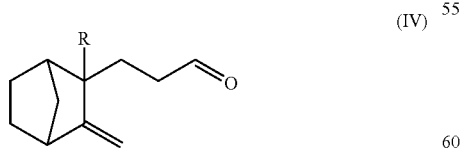
(IV)

in the form of any one of its stereoisomers or mixture thereof, and wherein R has the same meaning as in formula (II);

b) coupling said aldehyde (IV) with an aldehyde $R^1CH_2CHO$ (Aldol addition) to obtain an aldehyde (V)

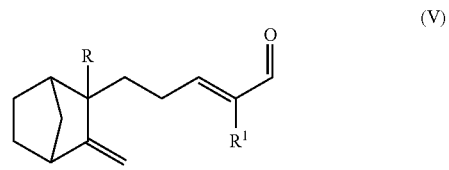
(V)

in the form of any one of its stereoisomers or mixture thereof, and wherein R and $R^1$ have the same meaning as in formula (II);

c) converting said compound (V) into the corresponding dienol derivative (VI)

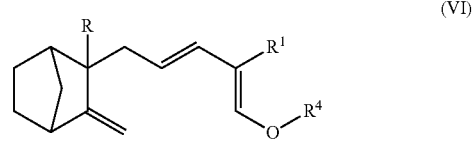
(VI)

in the form of any one of its stereoisomers or mixture thereof, and wherein R and $R^1$ have the same meaning as in formula (II), $R^4$ represents a $C_1$-$C_3$ alkyl, alkenyl or acyl group or a $C_3$-$C_8$ silyl group;

d) reducing the enolate (VI) into a compound (VII)

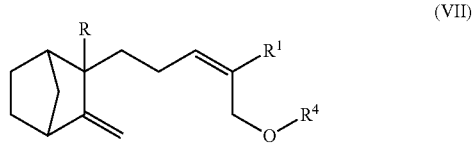
(VII)

in the form of any one of its stereoisomers or mixture thereof, and wherein R, $R^1$ and $R^4$ have the same meaning as in formula (VI);

e) optionally, transforming said compound (VII) into a compound (III")

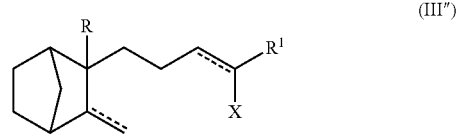
(III")

in the form of any one of its stereoisomers or mixture thereof, and wherein the dotted lines, R, $R^1$ and X have the same meaning as in formula (III).

Step e) is described as optional only because many of the compounds (VII) are already included in formula (III), and therefore, depending on the desired compound (III) the last step is not necessary.

According to a particular embodiment of the invention, said compounds (IV) to (VII) possess a configuration corresponding to the one described above for compounds (II') or (III').

Steps a) to e) can be performed according to standard methods well known by a person skilled in the art.

For instance, one may cite the following method for each step:
step a) or b) according to EP 10213;
step c) according to Simmons et al. in Helv. Chim. Acta, 1988, 71, 1000, or WO 2005/037243; and
step d) according to Shibasaki et al., in J. Org. Chem., 1988, 53, 1227 (where is reported the [1,4] hydrogenation of a dienol acetate derivative) or according to WO 08/120175.

An example of such procedure is provided in the Examples herein below.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 400 MHz or 125 MHz machine for $^1H$ or $^{13}C$ respectively, the chemical shifts δ are indicated in ppm with respect to TMS as standard, the coupling constants J are expressed in Hz.

Example 1

Preparation of a compound (I)—Method A:
a) Preparation of 3-exo-Methyl-bicyclo[2.2.1]heptan-2-one A solution of butyllithium in hexanes (1.58 M, 260.0 ml, 410.8 mmol) was added over a 40 minutes period to diisopropylamine (59.0 ml, 419.8 mmol) in solution in THF (100 ml) at −78° C. under nitrogen. The mixture was further stirred at −78° C. for 30 minutes, then (±)-norcamphor (40.118 g, 364.2 mmol) in THF (100 ml) was added dropwise at −78° C. and stirred for further 30 minutes at −78° C., before adding iodomethane (34.0 ml, 545.9 mmol). Once the addition was finished, the mixture was stirred for further 30 minutes at −78° C. and was allowed to reach room temperature. The mixture was hydrolyzed with a saturated aqueous solution of $NH_4Cl$. The aqueous layer was extracted twice with pentane, and the combined organic layers were washed with a saturated aqueous solution of $NH_4Cl$, a saturated aqueous solution of $NaHCO_3$ and brine. The organic layer was dried over $Na_2SO_4$, filtered off, and solvents were removed under slight vacuum to give a crude which was further purified by bulb to bulb distillation under reduced pressure to give the title compound (46.05 g) in quantitative yield.

$^1H$ NMR: 2.54 (br s, 1H), 2.32 (br s, 1H), 1.89-1.77 (m, 4H), 1.53-1.42 (m, 3H), 1.05 (d, J=7.6, 3H).
$^{13}C$ NMR: 220.9, 49.5, 48.3, 41.5, 34.4, 28.0, 23.8, 14.1.

b) Preparation of (3-exo-Methyl-bicyclo[2.2.1]hept-2-ylidene)-acetic acid

NaH (55%, 19.76 g, 451.45 mmol) and THF (400 ml) were placed in a reactor under nitrogen. Triethylphosphonoacetate (94.0 ml, 469.60 ml) was added to the suspension over a 25 minutes period at room temperature. The mixture was then heated at 50° C. for 45 minutes, 3-exo-methyl-bicyclo[2.2.1]heptan-2-one (46.054 g, 361.59 mmol) in THF (100 ml) was added to the ylide at 50° C. over a 25 minutes period. Once the addition finished, the mixture was refluxed for 2 hours. The mixture was then cooled down to room temperature and hydrolyzed with aqueous HCl 5% and ice. The mixture was extracted twice with $Et_2O$. The combined organic layers were washed with water, saturated aqueous $NaHCO_3$ and brine. The solution was dried over $Na_2SO_4$, filtered off and solvents were removed under vacuum to give a crude which was bulb to bulb distilled under reduced pressure to furnish a product containing 85.5% of (3-methyl-bicyclo[2.2.1]hept-2-ylidene)-acetic acid ethyl ester (76.36 g).

KOH pellets (36.31 g, 350.0 mmol) were dissolved in $H_2O$ (220 ml) at room temperature and (3-methyl-bicyclo[2.2.1]hept-2-ylidene)-acetic acid ethyl ester (76.361 g, 361.59 mmol) in absolute ethanol (500 ml) was added and the mixture was heated to reflux for 3.5 hours. The solution was allowed to reach room temperature and was extracted twice with pentane. The combined organic layers were washed with aqueous NaOH 5%, $H_2O$, and basic layers were acidified with concentrated HCl until pH=1. The acidic aqueous fraction was extracted twice with pentane, and the combined organic were washed with aqueous HCl 5%, $H_2O$, brine, dried over $Na_2SO_4$ and filtered off. Solvents were removed under vacuum to give a crude which was purified by bulb to bulb distillation under reduced pressure to afford the desired compound (46.575 g) in 75% yield over two steps.

$^1H$ NMR (E-isomer): 12.10 (br s, 1H), 5.72 (s, 1H), 2.80 (d, J=7.0, 2H), 2.10 (br s, 1H), 1.79-1.57 (m, 3H), 1.30-1.18 (m, 3H), 1.12 (d, J=7.0, 3H).
$^1H$ NMR (Z-isomer): 12.10 (br s, 1H), 5.53 (s, 1H), 3.97 (br s, 1H), 2.17 (d, J=7.2, 1H), 2.04 (br s, 1H), 1.79-1.57 (m, 3H), 1.30-1.18 (m, 3H), 1.03 (d, J=7.2, 3H).
$^{13}C$ NMR (E-isomer): 179.2, 172.4, 108.9, 47.7, 44.2, 43.8, 35.0, 29.8, 27.5, 17.2.
$^{13}C$ NMR (Z-isomer): 178.4, 172.7, 108.9, 45.5, 42.9, 41.9, 35.8, 28.1, 27.8, 19.1.

c) Preparation of 3(3-Methyl-bicyclo[2.2.1]hept-2-en-2-yl)-acetic acid

A solution of butyllithium in hexanes (1.40 M, 616.0 ml, 862.4 mmol) was added over a 60 minutes period to diisopropylamine (125.0 ml, 888.9 mmol) in THF (200 ml) at −78° C. under nitrogen. The mixture was further stirred at −78° C. for 30 minutes, then (3-methyl-bicyclo[2.2.1]hept-2-ylidene)-acetic acid (46.57 g, 280.2 mmol) in THF (200 ml) was added dropwise at −78° C. Once the addition finished the mixture was stirred for further 30 minutes at −78° C. and was allowed to reach room temperature. The orange mixture was hydrolyzed with aqueous HCl 5%. The aqueous layer was extracted twice with $Et_2O$, and the combined organic layers were washed twice with $H_2O$. The organic layer was extracted twice with aqueous NaOH 5% until pH=11, and the basic layers were acidified with concentrated HCl until pH=1. The aqueous fraction was extracted twice with $Et_2O$ and the combined organic fractions were washed with $H_2O$, brine, dried over $Na_2SO_4$ and filtered off. The solvents were removed under vacuum to give a crude which was further purified by bulb to bulb distillation under reduced pressure to afford the desired compound (42.24 g, 95% purity) in 86% yield.

$^1H$ NMR: 11.09 (br s, 1H), 3.12 (d of AB syst., J=15.2, 1H), 3.00 (d of AB syst., J=15.2, 1H), 2.80 (s, 1H), 2.62 (s, 1H), 1.66 (s, 3H), 1.63-1.61 (m, 2H), 1.40 (dt, $J^1$=8.1, $J^2$=2.0, 1H), 1.10-1.00 (m, 3H).
$^{13}C$ NMR: 178.6, 141.0, 131.5, 47.7, 46.8, 45.9, 32.6, 26.2, 25.4, 11.9.

d) Preparation of (±)-2-(3-Methyl-bicyclo[2.2.1]hept-2-en-2-yl)-ethanol

3(3-Methyl-bicyclo[2.2.1]hept-2-en-2-yl)-acetic acid (42.240 g, 254.2 mmol) in dry $Et_2O$ (500 ml) was added over a 60 minutes period to lithium aluminum hydride (14.99 g, 381.2 mmol) in $Et_2O$ (250 ml) under nitrogen at room temperature. Once the addition finished, the mixture was heated to reflux for 1.5 hours and was then cooled down to 0° C. The mixture was slowly hydrolyzed with 14.0 ml of $H_2O$ and 14.0 ml of aqueous NaOH 5%. Celite and $Na_2SO_4$ were added to the crude mixture. The suspension was filtered off through celite and solvent was removed under vacuum to give a crude which was further purified by bulb to bulb distillation under reduced pressure to afford the desired compound (42.24 g, 89% purity) in 76% yield.

$^1$H NMR: 3.66 (t, J=6.0, 2H), 2.70 (s, 1H), 2.61 (s, 1H), 2.37 (td, J$^1$=13.8, J$^2$=6.6, 1H), 2.20 (td, J$^1$=13.8, J$^2$=6.6, 1H), 1.65 (s, 3H), 1.64-1.62 (m, 2H), 1.44 (br s, 1H), 1.30 (dt, J$^1$=8.0, J$^2$=2.0, 1H), 1.06-1.01 (m, 3H).

$^{13}$C NMR: 140.4, 135.8, 61.1, 47.7, 46.9, 45.0, 30.3, 26.5, 25.4, 11.9.

e) Preparation of (±)-(3-Methyl-bicyclo[2.2.1]hept-2-en-2-yl)-acetaldehyde 2-(3-Methyl-bicyclo[2.2.1]hept-2-en-2-yl)-ethanol (16.37 g, 107.53 mmol) was dissolved in dichloromethane (150 ml) and Dess-Martin periodinane in solution in dichloromethane (15%, 536.2 g, 189.7 mmol) was added at room temperature over a 110 minutes period under nitrogen. The mixture was further stirred at room temperature for 30 minutes and was hydrolyzed with aqueous NaOH 5% in an ice-bath, and extracted 3 times with Et$_2$O. The combined organic layers were washed with H$_2$O, brine, dried over Na$_2$SO$_4$, and filtered off. Solvents were removed under reduced pressure to give a crude which was further purified by bulb to bulb distillation under reduced pressure to afford the desired compound (13.468 g, 88% purity) in 83% yield.

$^1$H NMR: 9.57 (t, J=2.6, 1H), 3.15 (dd, J$^1$=16, 1H), 3.05 (d, J=16, 1H), 2.68 (d, J=14.3, 2H), 1.67 (s, 3H), 1.65-1.63 (m, 2H), 1.42-1.39 (m, 1H), 1.09-1.01 (m, 3H).

$^{13}$C NMR: 199.7, 142.5, 130.1, 47.8, 46.9, 46.0, 42.8, 26.2, 25.3, 12.1.

f) Preparation of (±)-1-(3-Methyl-bicyclo[2.2.1]hept-2-en-2-yl)-but-3-yn-2-ol

Ethynylmagnesium bromide in THF (0.5 M, 210.0 ml, 105.0 mmol) was placed in a reactor under a nitrogen atmosphere at room temperature and (3-Methyl-bicyclo[2.2.1]hept-2-en-2-yl)-acetaldehyde (12.15 g, 80.9 mmol) in THF (200 ml) was introduced over a 90 minutes period and the mixture turned orange. The mixture was further stirred at room temperature for 30 minutes and was hydrolyzed with aqueous HCl 5% at room temperature. The mixture was extracted twice with Et$_2$O and the combined organic layers were washed twice with a saturated aqueous solution of NaHCO$_3$, H$_2$O, and brine and dried over Na$_2$SO$_4$. Solvents were removed under vacuum to give a crude which was purified by flash chromatography with cyclohexane/AcOEt (95/5) as eluent to afford the title compound (11.32 g) in 79% yield.

$^1$H NMR (isomer A): 4.44 (br s, 1H), 2.76 (s, 1H), 2.63 (s, 1H), 2.52 (dd, J$^1$=13.8, J$^2$=8.1, 1H), 2.40 (d, J=2.0, 1H), 2.44 (dd, J$^1$=13.8, J$^2$=5.9, 1H), 1.98 (br s, 1H), 1.67 (s, 3H), 1.64-1.62 (m, 2H), 1.34-1.32 (m, 1H), 1.11-1.00 (m, 3H).

$^1$H NMR (isomer B): 4.46 (br s, 1H), 2.86 (s, 1H), 2.62 (s, 1H), 2.53 (dd of AB syst., J$^1$=13.8, J$^2$=6.3, 1H), 2.43 (d, J=2.1, 1H), 2.39 (dd of AB syst., J$^1$=13.8, J$^2$=5.7, 1H), 2.03 (br s, 1H), 1.67 (s, 3H), 1.64-1.62 (m, 2H), 1.39-1.36 (m, 1H), 1.11-1.01 (m, 3H).

$^{13}$C NMR (isomer A): 142.2, 134.4, 84.8, 72.6, 60.9, 47.7, 46.9, 45.2, 35.7, 26.4, 25.2, 12.0.

$^{13}$C NMR (isomer B): 141.9, 134.6, 85.1, 72.7, 61.3, 47.8, 46.9, 46.0, 35.1, 26.5, 25.3, 12.1.

Preparation of a compound (I)—Method B a) Preparation of 3-Methylene-bicyclo[2.2.1]heptan-2-one Diethylamine (50.0 ml, 455.0 mmol) was added over a 15 min. period to formaldehyde (36% in MeOH/H$_2$O, 50.0 ml, 1.82 mol) at 0° C. The resultant mixture was treated with a 33 minutes period with acetic acid (50.0 ml, 910.0 mmol). Once the addition was finished, the temperature was increased to room temperature and the mixture was added over a 22 minutes period to (±)-norcamphor (50.0 g, 0.455 mol) in the presence of a small amount of BHT at 95° C. The mixture was refluxed for 5 hours and cooled down to room temperature. The yellow mixture was hydrolyzed with aqueous HCl 5% and ice (pH=1). The aqueous layer was extracted twice with Et$_2$O, and the combined organic layers were washed with H$_2$O, aqueous NaOH 5% and twice with brine, dried over Na$_2$SO$_4$ and filtered off. Et$_2$O was distilled under atmospheric pressure to give a crude which was further purified by bulb to bulb distillation under reduced pressure to afford the desired compound (26.800 g) in 48% yield.

$^1$H NMR: 5.72 (s, 1H), 5.16 (s, 1H), 3.13 (br s, 1H), 2.73 (d, J=2.8, 1H), 1.90-1.86 (m, 2H), 1.77-1.73 (m, 1H), 1.64-1.61 (m, 1H), 1.57-1.53 (m, 2H).

$^{13}$C NMR: 205.8, 150.1, 111.7, 49.2, 42.5, 36.8, 28.1, 23.6.

b) Preparation of (±)-3-endo-Methyl-bicyclo[2.2.1]heptan-2-one

3-Methylene-bicyclo[2.2.1]heptan-2-one (29.670 g at 64.4%, 0.157 mmol) was hydrogenated (atmospheric pressure) in presence of Pd/C (10% in Pd, 1.480 g, 5% w/w) in Et$_2$O (300 ml) at room temperature for 2 hours. The mixture was filtered through "filter cel" and Et$_2$O was removed by distillation to give a crude which was further purified by distillation (20 mbar, 87-88° C.) to afford the title compound (19.82 g) in quantitative yield.

$^1$H NMR: 2.60 (d, J=4.8, 1H), 2.53 (s, 1H), 2.15-2.08 (m, 1H), 1.86-1.77 (m, 1H), 1.72-1.68 (m, 1H), 1.65-1.56 (m, 3H), 1.43-1.36 (m, 1H), 1.02 (d, J=7.2, 3H).

$^{13}$C NMR: 220.6, 50.3, 48.3, 40.5, 37.2, 25.4, 21.0, 10.8.

c) Preparation of (±)-2-endo-Methyl-3-methylene-bicyclo[2.2.1]heptane: by a Wittig reaction Methyltriphenylphosphonium bromide (13.31 g, 36.9 mmol) in THF (40.0 ml) was treated in one portion with t-BuOK (6.910 g, 61.6 mmol) at room temperature under nitrogen. The resultant yellow mixture was stirred at room temperature and 3-methyl-bicyclo[2.2.1]heptan-2-one (4.0 g, 30.8 mmol) in THF (16.0 ml) was added over a 8 minutes period and was stirred at room temperature for 15 minutes. The mixture was poured over a saturated aqueous solution of ammonium chloride and was extracted twice with pentane. The combined organic layers were washed with water and brine, dried over Na$_2$SO$_4$ and filtered off. Solvents were removed by distillation at atmospheric pressure and the crude mixture was further purified by bulb to bulb distillation to afford the desired compound (2.845 g) as colourless oil in 76% yield.

$^1$H NMR: 4.77 (d, J=2.7, 1H), 4.51 (s, 1H), 2.66 (d, J=3.6, 1H), 2.37-2.34 (m, 1H), 2.15 (br s, 1H), 1.67-1.52 (m, 2H), 1.45-1.30 (m, 3H), 1.22-1.16 (m, 1H), 1.02 (d, J=7.0, 3H).

$^{13}$C NMR: 161.7, 100.3, 46.5, 42.3, 41.34, 39.5, 30.8, 21.4, 15.1.

d) Preparation of trimethylsilyl-propynal

Trimethylsilylethyne (5.0 ml, 36.10 mmol) in THF (25.0 ml) was dropwise added to a solution of EtMgBr in THF (1M, 44.0 ml, 44.0 mmol) at 10-15° C. under nitrogen. Once the addition finished, the mixture was stirred at room temperature for one hour and was added over a 30 min. period to an efficiently stirred mixture of DMF (10.0 ml, 123.0 mmol) in Et$_2$O (20.0 ml) at −25° C. The white suspension was allowed to reach room temperature, stirred for one hour, heated at 30° C. for 15 minutes, and poured into H$_2$SO$_4$ 5% at 0° C. The aqueous layer was extracted three times with Et$_2$O, the combined organic layers were washed with a saturated aqueous solution of NH$_4$Cl, dried over Na$_2$SO$_4$, and the solvents were carefully removed under vacuum to give a crude which was further purified by bulb to bulb distillation (20 mBar, room temperature) to afford the title compound (2.255 g) in 49% yield.

$^1$H NMR: 9.15 (s, 1H), 0.25 (s, 9H).
$^{13}$C NMR: 176.7, 103.0, 102.3, 0.88.

e) Preparation of 1-(3-Methyl-bicyclo[2.2.1]hept-2-en-2-yl)-4-trimethylsilanyl-but-3-yn-2-ol via ene-reaction Me$_2$AlCl (1M in hexanes, 1.1 ml, 1.1 mmol) was dropwise added to a solution of trimethylsilyl-propynal (154.0 mg, 1.22 mmol) and 2-endo-methyl-3-methylene-bicyclo[2.2.1]heptane (140.0 mg, 1.15 mmol) in dichloromethane (5.0 ml) at −78° C. under nitrogen. The mixture was stirred at −78° C. for 15 minutes and was hydrolyzed with aqueous HCl 5%. The temperature was then slowly allowed to increase to room temperature and extracted twice with CH$_2$Cl$_2$. The combined organic layers were washed with water, brine, dried over Na$_2$SO$_4$ and filtered off to give a crude which was further purified by flash chromatography with cyclohexane/AcOEt (97/3) as eluent to afford title compound (148.0 mg) in 59% yield.

Ene-reaction could also be performed at −78° C. with BF$_3$.Et$_2$O (5 mol %) as catalyst in dichloromethane at −78° C. with complete conversion in 5 minutes.

f) Preparation of 1-(3-Methyl-bicyclo[2.2.1]hept-2-en-2-yl)-but-3-yn-2-ol

Simple treatment of 1-(3-Methyl-bicyclo[2.2.1]hept-2-en-2-yl)-4-trimethylsilanyl-but-3-yn-2-ol with an excess of K$_2$CO$_3$ in methanol for 1 hour at room temperature afforded 1-(3-methyl-bicyclo[2.2.1]hept-2-en-2-yl)-but-3-yn-2-ol in quantitative yield.

$^1$H NMR: 4.42 (dd, J$^1$=J$^2$=7.0, 1H), 2.75 (s, 1H), 2.60 (s, 1H), 2.52-2.47 (m, 1H), 2.42-2.35 (m, 1H), 1.91 (br s, 1H), 1.66 (s, 3H), 1.62-1.60 (m, 2H), 1.34-1.32 (m, 1H), 1.11-0.99 (m, 3H), 0.15 (s, 9H). $^{13}$C NMR: 141.8, 134.7, 106.8, 89.3, 61.7, 47.8, 47.1, 45.6, 36.0, 26.6, 25.3, 12.1, 10.0.

Example 2

Preparation of a Compound (II)

a) Preparation of 3-(2-Methyl-3-methylene-bicyclo[2.2.1]hept-2-exo-yl)-propen-1-al with CuBF$_4$(CH$_3$CN)$_4$ CuBF$_4$(CH$_3$CN)$_4$ (0.294 g, 0.93 mmol) was added to a two-rounded bottom flask charged with 1-(3-Methyl-bicyclo[2.2.1]hept-2-en-2-yl)-but-3-yn-2-ol (3.24 g, 18.4 mmol) in solution in 1,2-dichloroethane (100 ml) at room temperature under nitrogen. The mixture was stirred at 50° C. for 140 minutes. The crude mixture was allowed to reach room temperature and was filtered through a short pad of silica gel with CH$_2$Cl$_2$ as eluent. Solvents were removed under vacuum to give a crude which was further purified by bulb to bulb distillation under reduced pressure to afford the title compound (3.12 g) in 96% yield.

$^1$H NMR: 9.52 (d, J=7.8, 1H), 6.77 (d, J=15.7, 1H), 6.09 (dd, J$^1$=15.7, J$^2$=7.8, 1H), 5.01 (s,1H), 4.58 (s, 1H), 2.76 (br s, 1H), 2.18 (br s, 1H), 1.80-1.69 (m, 2H), 1.58-1.52 (m, 2H), 1.37-1.30 (m, 1H), 1.27-1.24 (m, 1H), 1.23 (s, 3H).

$^{13}$C NMR: 194.5, 165.4, 160.4, 130.1, 104.1, 49.7, 46.5, 46.3, 37.1, 29.8, 23.0, 22.7.

b) Preparation of 3-(2-Methyl-3-methylene-bicyclo[2.2.1]hept-2-exo-yl)-propen-1-al with AgBF$_4$ AgBF$_4$ (20.0 mg, 0.10 mmol) was added to a two-rounded bottom flask charged with 1-(3-methyl bicyclo[2.2.1]hept-2-en-2-yl)-but-3-yn-2-ol (371.0 mg, 2.10 mmol) in solution in 1,2-dichloroethane (10 ml) at room temperature under nitrogen. The mixture was stirred at 50° C. for 80 minutes in the dark. The crude mixture was allowed to reach room temperature and was filtered through a short pad of silica gel with CH$_2$Cl$_2$ as eluent. Solvents were removed under vacuum to give a crude which was further purified by flash chromatography with cyclohexane/AcOEt (97/3) as eluent to afford the title compound (172.0 mg) in 46% yield.

c) Preparation of 3-(2-Methyl-3-methylene-bicyclo[2.2.1]hept-2-exo-yl)-propen-1-al with AgNO$_3$ in presence of KNO$_3$ as additive AgNO$_3$ (17.6 mg, 0.10 mmol) and KNO$_3$ (107.0 mg, 1.06 mmol) was added to a two-rounded bottom flask charged with 1-(3-methyl bicyclo[2.2.1]hept-2-en-2-yl)-but-3-yn-2-ol (181.0 mg, 1.03 mmol) in solution in THF/H$_2$O (2/1, 10 ml) at room temperature under nitrogen. The mixture was stirred at reflux for 6.5 hours in the dark and AgNO$_3$ (18.5 mg, 0.11 mmol) was added to the mixture before being cooled down to room temperature and stirred overnight in the dark. The crude mixture was diluted with Et$_2$O (10 ml) and the aqueous layer was extracted with Et$_2$O. The combined organic layers were filtered through a short pad of silica gel with CH$_2$Cl$_2$ as eluent. Solvents were removed under vacuum to give a crude which was further purified by flash chromatography with cyclohexane/AcOEt (95/5) as eluent to afford the title compound (115.0 mg) in 64% yield.

Example 3

Preparation of a Compound (III) and of Derivatives Thereof a) Preparation of a compound (IV): 3-(2-Methyl-3-methylene-bicyclo[2.2.1]hept-2-exo-yl)-propan-1-al Pd/CaCO$_3$ (5% w/w, 93.0 mg) was placed into a two neck round bottom flask in methanol (30 ml) and the atmosphere was purged with N$_2$ before adding 3-(2-methyl-3-methylene-bicyclo[2.2.1]hept-2-exo-yl)-propen-1-al (1.886 g, 10.70 mmol). The atmosphere was further purged with nitrogen followed with hydrogen at room temperature. The mixture was stirred at room temperature under one atmosphere of hydrogen for 4.5 hours. The mixture was filtered through "filter cel" to give a crude which was further purified by flash chromatography with pentane/Et$_2$O (97/3) as eluent to afford the title compound (1.627 g) in 85% yield.

$^1$H NMR: 9.78 (t, J=1.9, 1H), 4.79 (s, 1H), 4.49 (s, 1H), 2.69 (d, J=3.9, 1H), 2.49-2.41 (m, 2H), 2.02 (br s, 1H), 1.75-1.54 (m, 5H), 1.47-1.38 (m, 1H), 1.28-1.19 (m, 2H), 1.02 (s, 3H).

$^{13}$C NMR: 202.8, 165.0, 100.6, 46.7, 45.0, 44.1, 40.1, 37.0, 32.6, 29.6, 23.6, 22.5.

A) Preparation of β-santalol (via Wittig and hydroxyalkylation reaction)

A solution of butyllithium in hexanes (1.35 M, 11.7 ml, 15.8 mmol) was added over a 15 minutes period to a stirred suspension of ethyltriphenylphosphonium iodide (6.61 g, 15.8 mmol) in THF (125 ml) at 0° C. The resultant red solution was cooled to −78° C. and 3-(2-methyl-3-methylene-bicyclo[2.2.1]hept-2-exo-yl)-propanal (2.55 g, 14.33 mmol) in solution in THF (16 ml) was added over a 15 minutes period. After further 5 minutes at −78° C., a solution of butyllithium in hexanes (1.35 M, 12.7 mL, 17.2 mmol) was added over a 5 minutes period and the mixture was further stirred for 20 minutes at −78° C. before allowing to reach 0° C. in 2 hours. Dry paraformaldehyde (2.60 g, 86.0 mmol) was added in one portion to the deep red homogeneous solution and the mixture was stirred for 30 minutes at 0° C. and was allowed to reach room temperature. After 1 hour at room temperature the mixture was poured into 5.2 ml of saturated aqueous solution of NH$_4$Cl and extracted twice with CH$_2$Cl$_2$. The organic layer was washed with water and brine, and dried with $Na_2SO_4$. The mixture was filtered through a short pad of silica gel with dichloromethane as eluent and solvents were removed under pressure to give a crude. Purification of crude compound was performed by flash chromatography on silica gel with cyclohexane/AcOEt 90/10) as eluent to give pure β-santalol as pale yellow oil. Further bulb to bulb distillation under reduced pressure afforded β-santalol in 50% yield (Z:E=95:5).

$^1$H NMR (CDCl$_3$, 400 MHz): 5.29 (t, J=7.5, 1H), 4.73 (s, 1H), 4.45 (s, 1H), 4.14 (s, 2H), 2.66 (d, J=3.8, 1H), 2.12-1.94 (m, 3H), 1.78 (d, J=1.2, 3H), 1.71-1.60 (m, 3H), 1.44-1.36 (m, 2H), 1.32 (br s, 1H), 1.27-1.17 (m,3H), 1.04 (s, 3H).

$^{13}$C NMR (CDCl$_3$, 125 MHz): 166.2, 133.9, 129.0, 99.7, 61.6, 46.8, 44.7, 44.6, 41.5, 37.1, 29.7, 23.7, 23.2, 22.6, 21.2.

B) Preparation of β-santalol (via [1,4] hydrogenation)
i) Preparation of a compound (V): 2-methyl-5-(2-methyl-3-methylene-bicyclo[2.2.1]hept-exo-2-yl)-pent-2-enal 3-(2-Methyl-3-methylene-bicyclo[2.2.1]hept-2-exo-yl)-propan-1-al (274.0 mg, 1.54 mmol) was dissolved in toluene (15.0 ml) at room temperature under nitrogen. The mixture was heated to reflux and propionaldehyde (0.4 ml, 1.96 mmol) and aqueous catalytic solution of hexamethyleneimine and benzoic acid (0.12 ml, 0.616 mmol) was separately added in one portion. Once that addition was finished, the mixture was further heated at reflux for 6 hours. The mixture was cooled down to room temperature and extracted twice with brine, the organic layer was dried over MgSO$_2$, filtered off and concentrated to give a crude which was further purified by flash chromatography with cyclohexane/AcOEt (95/5) to afford the title compound in 80% yield.

$^1$H NMR: 9.38 (s, 1H), 6.48 (dt, J$^1$=7.5, J$^2$=1.2, 1H), 4.78 (s, 1H), 4.49 (s, 1H), 2.69 (d, J=3.9, 1H), 2.40-2.29 (m, 2H), 2.12 (d, J=3.1, 1H), 1.75 (s, 3H), 1.72-1.64 (m, 3H), 1.59-1.51 (m, 1H), 1.47-1.36 (m, 2H), 130-1.21 (m, 2H), 1.09 (s, 3H).

$^{13}$C NMR: 195.2, 165.5, 155.2, 139.1, 100.3, 46.8, 44.8, 44.7, 39.4, 37.1, 29.6, 24.9, 23.7, 22.6, 9.1.

ii) Preparation of a compound (IV): Acetic acid 2-methyl-5-(2-methyl-3-methylene-bicyclo[2.2.1] hept-2-exo-yl)-penta-1,3-dienyl ester To a stirred solution of 2-methyl-3-methyl-3-methylene-bicyclo[2.2.1]hept-2-yl)-pent-2-enal (268.0 mg, 1.23 mmol) in toluene (3.0 ml) were added Ac$_2$O (0.35 ml, 3.70 mmol), Et$_3$N (0.70 ml, 5.02 mmol), and a catalytic amount of DMAP (15.0 mg, 0.1 mmol). The resulting mixture was heated to reflux for 22 hours. The mixture was cooled down to room temperature and quenched with brine, extracted twice with Et$_2$O, dried over MgSO$_4$, filtered off and concentrated to give a crude which was further purified by flash chromatography with cyclohexane/AcOEt (98/2) to afford the title compound in 82% yield (E:Z=79:21).

$^1$H NMR: 7.18 (s, 1H), 5.99 (d, J=12.4, 1H), 5.72 (dt, J$^1$=12.4, J$^2$=6.1, 1H), 4.76 (s, 1H), 4.47 (s, 1H), 2.68 (d, 3.4, 1H), 2.17 (s, 3H), 2.12-2.01 (m, 2H), 1.81 (d, J=1.0, 3H), 1.73-1.63 (m, 3H), 1.43-1.39 (m, 2H), 1.27-1.18 (m, 2H), 1.02 (s, 3H).

$^{13}$C NMR: 167.9, 165.5, 134.4, 130.6, 126.9, 120.7, 100.0, 46.9, 45.3, 45.0, 44.5, 37.0, 29.7, 23.6, 23.0, 20.8, 10.4.

iii) Preparation of (2Z)-Acetic acid 2-methyl-5-(2-methyl-3-methylene-bicyclo[2.2.1]hept-2-exo-yl)-pent-2-enyl ester (VII)

Acetic acid 2-methyl-3-methyl-3-methylene-bicyclo [2.2.1]hept-2-exo-yl)-penta-1,3-dienyl ester (6.80 g, 93% pure; 24.3 mmol 0.18 mmol) was treated with [(Cp*)Ru (COD)]BF$_4$ (52 mg, 0.122 mmol) and maleic acid (230 mg, 1.95 mmol) in dry and degassed acetone (20 ml) at 60° C. under 4 bars of H$_2$ for 24 hours. The product was extracted with pentane/5% NaOH, washed twice with saturated aqueous NaCl, dried (Na$_2$SO$_4$) and bulb-to-bulb distilled: 6.80 g (81% Z and 5% E by GC; 92%).

$^1$H NMR: 5.38 (t, J=7.1, 1H), 4.73 (s, 1H), 4.59 (s, 1H), 4.45 (s, 1H), 2.66 (br s, 1H), 2.12-2.04 (m, 4H), 2.07 (s, 3H), 1.73 (d, J=1.0, 3H), 1.69-1.61 (m, 3H), 1.45-1.37 (m, 2H), 1.27-1.17 (m, 3H), 1.04 (m, 3H).

$^{13}$C NMR: 171.1, 166.1, 131.4, 129.4, 99.7, 63.2, 46.8, 44.7, 44.6, 41.2, 37.1, 29.7, 23.7, 23.4, 22.6, 21.5, 21.0.

iv) Preparation of and β-santalol (III)

Simple treatment with an excess of K$_2$CO$_3$ in methanol for 1 hour at room temperature afforded β-santalol in quantitative yield.

C) Preparation of Compounds (III) with All Dotted Lines Being C═C i) Preparation of 2-Methyl-5-(2-methyl-3-methylene-bicyclo [2.2.1]hept-2-exo-yl)-penta-2,4-dienoic acid ethyl ester NaH (55%, 168.0 mg, 3.85 mmol) and THF (5.0 ml) were placed in a reactor and 2-(diethoxy-phosphoryl)-propionic acid ethyl ester (939.0 mg, 3.94 mmol) was added dropwise at room temperature to the suspension over a 10 minutes period. The mixture was heated at 50° C. for 45 minutes 3-(2-methyl-3-methylene-bicyclo[2.2.1]hept-2-exo-yl)-propen-1-al (566.0 mg, 3.21 mmol) in THF (2.0 ml) was added dropwise to the glide at 50° C. Once the addition finished, the mixture was refluxed for 1 hour. The mixture was then cooled down to room temperature and hydrolyzed with aqueous HCl 5%. The reaction was extracted twice with Et$_2$O. The combined organic layers were washed with water, aqueous saturated NaHCO$_3$ and brine. The solution was dried over Na$_2$SO$_4$, filtered off and solvents were removed under vacuum to give a crude which was further purified by bulb to bulb distillation under reduced pressure to afford the title compound (651.0 mg) in 78% yield.

$^1$H NMR: 7.18 (d, J=11.2, 1H), 6.31 (dd, J$^1$=15.2, J$^2$=11.2, 1H), 6.05 (d, J=15.2, 1H), 4.98 (s, 1H), 4.56 (s, 1H), 4.20 (q, J=7.1, 2H), 2.73 (d, J=3.2, 1H), 2.09 (d, J=3.1, 1H), 1.92 (d, J=1.2, 3H), 1.73-1.65 (m, 2H), 1.61-1.57 (m, 1H), 1.52-1.43 (m, 1H), 1.34-1.27 (m, 1H), 1.29 (t, J=7.1, 3H), 1.19-1.18 (m, 1H), 1.18 (s, 3H).

$^{13}$C NMR: 168.6, 161.8, 150.2, 138.8, 125.5, 123.0, 103.2, 60.4, 49.6, 47.0, 46.4, 37.1, 30.1, 23.5, 23.0, 14.3, 12.7.

ii) Preparation of 2-Methyl-5-(2-methyl-3-methylene-bicyclo[2.2.1]hept-2-exo-yl)-pent-2.4-dien-1-ol Dibal-H (1M in toluene, 5.5 ml, 5.5 mmol) was added over a 25 minutes period to a stirred solution of 2-methyl-5-(2-methyl-3-methylene-bicyclo[2.2.1]hept-2-exo-yl)-penta-2,4-dienoic acid ethyl ester (651.0 mg, 2.50 mmol) in dichloromethane (20.0 ml) at −78° C. under nitrogen.

The resulting mixture was stirred at −78° C. for 70 minutes and was placed at 0° C. to be quenched with aqueous HCl 5% and brine. The mixture was extracted twice with CH$_2$Cl$_2$, dried over Na$_2$SO$_4$, filtered off and concentrated to afford a crude which was further purified by flash chromatography with cyclohexane/AcOEt (9/1) as eluent to afford the title compound (453.0 mg) in 83% yield.

$^1$H NMR: 6.22 (dd, J$^1$=12.2, J$^2$=8.6, 1H), 6.03 (d, J=8.6, 1H), 5.69 (d, J=12.2, 1H), 4.95 (s, 1H), 4.54 (s, 1H), 4.05 (s, 2H), 2.71 (d, J=2.7, 1H), 2.04 (br s, 1H), 1.78 (s, 3H), 1.71-1.62 (m, 3H), 1.58 (br s, 1H), 1.42-1.49 (m, 1H), 1.31-1.26 (m, 1H), 1.17-1.15 (m, 1H), 1.16 (s, 3H).

$^{13}$C NMR: 162.4, 142.9, 135.2, 125.7, 122.9, 102.6, 68.8, 49.1, 47.2, 46.5, 37.1, 30.2, 23.9, 23.0, 14.3.

Example 4

Preparation of (−)-β-Santalol a) Preparation of (1S,2S,4R)-2-methyl-3-methylene-bicyclo[2.2.1]heptane: by enantioselective and exo-selective Diels-Alder reaction (according to MacMillan et coll., J. Am. Chem. Soc. 2000, 122, 4243 and PCT Int. Appl. 2003002491)

A solution of (2S,5S)-(−)-2-tert-butyl-3-methyl-5-benzyl-4-imidazolidinone.HCl (0.1 equiv) in MeOH/water (95:5) was treated with cyclopentadiene (3 molar equivalents) and crotonaldehyde (1 molar equivalent) for 24 hours at room temperature. The 72:28 mixture of exo- and endo cycloadducts (both 71% ee) (exo/endo with respect to CHO)) was reduced with LiAlH$_4$ (1 molar equivalent) in Et$_2$O at 25 to 30° C. to afford the corresponding exo- and endo-methyl-norbornenols in 30% yield (2 steps). These compounds could be separated by chiral SFC (supercritical fluid chromatography: OD-H column; co-solvent: MeOH: 5% (2 min), then +1% MeOH/min; flow: 2 ml/min; 200 bar; $1^{st}$ peak exo major, $2^{nd}$ peak exo minor, $3^{rd}$ peak endo major, $4^{th}$ peak endo minor). Enantiomeric enrichment of these known compounds can be effected by crystallization (Seebach et coll., J. Org. Chem. 1995, 60, 1788). The exo-enriched methyl-norbornenol was hydrogenated (5% of 10% Pd on C; Et$_2$O, 99% yield). The exo-enriched methyl norbornanol was treated with Ac$_2$O (1.2 molar equivalents), NEt$_3$ (2.0 molar equivalents), 4-dimethylaminopyridine (5 mol %), toluene at 0° C. for 17 hours to afford the exo-enriched acetate in 74% yield. The compound so obtained was diluted in pentane (5%) and pyrolyzed at 610° C. through a 30 cm column filled with quartz pieces under a nitrogen flow to afford the optically active endo-enriched title compound in ca. 80% yield.

Note: This compound (but exo-enriched) was also prepared by Joachimsmann-Dufresne, Blanchard, Bull. Soc. Chim. France 1968, 385 by pyrolysis of the corresponding acetate (longer column, 510° C.). In fact, Blanchard et coll. (Bull. Soc. Chim. France 1968, 385; Bull. Soc. Chim. France 1972, 4770) prepared the title compound (exo-enriched and racemic) from cyclopentadiene and crotonaldehyde and the reduction/hydrogenation was performed in one step (H$_2$, Raney-Ni, 90 bar, 110° C.).

The title compound thus obtained had a NMR characterisation corresponding to the one of the compound obtained Example 1, method B, c).

a') Preparation of (1S,2S,4R)-2-methyl-3-methylene-bicyclo[2.2.1]heptane: by enantioselective and exo-selective Diels-Alder reaction (according to Hayashi et al., Angew. Chem. Int. Ed. 2008, 47, 6634)

A heterogeneous mixture of (S)-(+)-2-[bis-(3,5-trifluoromethylphenyl)trimethylsilyloxy-methyl]pyrrolidinium perchlorate (5 mol %), water, freshly distilled crotonaldehyde (1 molar equivalent) and cyclopentadiene (3 molar equivalents) was stirred for 24 hours at room temperature. The 72:28 mixture of exo- and endo cycloadducts (95 respectively 76% ee) (exo/endo with respect to CHO)) was reduced with NaBH$_4$ (1 molar equivalent) in MeOH at 25 to 30° C. to afford the corresponding exo- and endo-methyl-norbornenols in 49% yield (2 steps). The enantiomeric excesses of these compounds were determined by chiral GC of the corresponding trifluoroacetates (Seebach et coll., J. Org. Chem. 1995, 60, 1788) using a chiral capillary column (CP-Chirasil-DEX CB (25×0.25 mm, Chrompack). The methyl-norbornenols were hydrogenated (5% of 10% Pd on C; Et$_2$O, 99% yield). Treatment of the methyl norbornanols with ClCOOEt (2 molar equivalents), pyridine (2.0 molar equivalents) and toluene at 0° C. for 90 min and at room temperature for 30 min afforded the corresponding methyl carbonates in 91% yield. The compound thus obtained was diluted in pentane (5%) and pyrolyzed at 415° C. through a 3 m column under a nitrogen flow to afford the optically active endo-enriched title compound in ca. 90% yield and 91% ee (chiral GC: first peak major (bad separation) together with the exo-compound (endo/exo=72:28; exo: ca. 54% ee (second peak major)).

The title compound thus obtained had NMR characterisation corresponding to the one of the compound obtained Example 1, method B, c).

b) Preparation of (1R,4S)-1-(3-Methyl-bicyclo[2.2.1]hept-2-en-2-yl)-but-3-yn-2-ol: via ene-reaction Me$_2$AlCl (1M in hexanes, 23.7 ml, 23.7 mmol) was added dropwise to a solution of trimethylsilyl-propynal (3.74 g; 80% pure, 23.7 mmol) and (1S,2S,4R)-2-endo-methyl-3-methylene-bicyclo[2.2.1]heptane (4.25; 65% pure; containing 25% of exo-isomer; 22.6 mmol) in dichloromethane (80 ml) containing a few crystals of BHT at −78° C. under nitrogen. The mixture was stirred at −78° C. for 15 minutes and was poured into aqueous HCl 5%. The product was extracted with ether. The combined organic layers were washed with water, conc. NaHCO$_3$ solution, brine, dried over Na$_2$SO$_4$ and filtered off to give a crude which was bulb-to-bulb distilled (0.07 mbar/ oven temp. 120° C.) to afford (1R,4S)-1-(3-methyl-bicyclo[2.2.1]hept-2-en-2-yl)-4-trimethylsilanyl-but-3-yn-2-ol (4.84 g; 66% pure). It was dissolved in MeOH (50 ml) and treated with K$_2$CO$_3$ (3.23 G, 23.4 mmol) for 30 min at room temperature. Usual extraction (pentane/water) and bulb-to-bulb distillation afforded the title compound (3.09 g). Flash chromatography (SiO$_2$; cyclohexane/AcOEt=9:1) afforded pure title compound (2. 62 g; 66%). The title compound thus obtained had NMR characterisation corresponding to the one of the compound obtained Example 1, method A, f).

c) Preparation of (1S,2S,4R)-3-(2-Methyl-3-methylene-bicyclo[2.2.1]hept-2-exo-yl)-propen-1-al with CuBF$_4$(CH$_3$CN)$_4$ It was proceeded as described above for the racemic compound (see Example 2, a). Starting from (1R,4S)-1-(3-methyl-bicyclo[2.2.1]hept-2-en-2-yl)-but-3-yn-2-ol (2.02 g; 11.5 mmol), 1.91 g (94%) of the title compound were obtained. Chiral GC: 91% ee (first peak major). Low-temperature crystallization afforded the title compound with 97% ee (1.67 g).

$[\alpha]_D^{20}$: −267.4 (CHCl$_3$; c=1.06).

The title compound thus obtained had NMR characterisation corresponding to the one of the compound obtained Example 2, a).

d) Preparation of (1S,2R,4R)-3-(2-Methyl-3-methylene-bicyclo[2.2.1]hept-2-exo-yl)-propan-1-al It was proceeded as described above for the racemic compound (see Example 3, a), but MeOH/water (96:4) was used as the solvent.

Starting from (1S,2S,4R)-3-(2-methyl-3-methylene-bicyclo[2.2.1]hept-2-exo-yl)-prop en-1-al (894 mg; 5.08 mmol), 769 mg (85%) of the title compound were obtained. No separation by chiral GC.

$[\alpha]_D^{20}$: −112.3 (CHCl$_3$; c=0.86).

The title compound thus obtained had NMR characterisation corresponding to the one of the compound obtained Example 3, a).

e) Preparation of (1S,2R,4R)-2-methyl-5-(2-methyl-3-methylene-bicyclo[2.2.1]hept-exo-2-yl)-pent-2-enal It was proceeded as described above for the racemic compound (see Example 3, B) i)) Starting from (1S,2R,4R)-3-(2-methyl-3-methylene-bicyclo[2.2.1]hept-2-exo-yl)-propan-1-al, the title compound was obtained in 92% purity and 90% yield. No separation by chiral GC.

$[\alpha]_D^{20}$: −99.8 (CHCl$_3$; c=1.14).

The title compound thus obtained had NMR characterisation corresponding to the one of the compound obtained (see Example 3, B) i))

f) Preparation of and (−)-β-santalol

Application of the procedure for the racemic compound (via compounds IV and VII) (see Example 3, B) afforded (−)-β-santalol as a 94/6 Z/E-mixture in 80% yield. Pure Z-(−)-β-santalol of 97% ee was obtained by chromatography (SiO$_2$; cyclohexane/AcOEt=9:1).

$[\alpha]_D^{20}$: −104.3 (CHCl$_3$; c=0.76).

The title compound thus obtained had NMR characterisation corresponding to the one of the compound obtained Example 3, B).

What is claimed is:

1. A dienol compound of formula

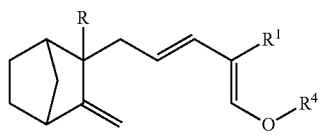

(VI)

in the form of any one of its stereoisomers or mixture thereof, wherein R represents a methyl or ethyl group; $R^1$ represents a hydrogen atom or a methyl or ethyl group; $R^4$ represents a $C_1$-$C_3$ alkyl, alkenyl or acyl group or a $C_3$-$C_8$ silyl group.

2. The compound of claim 1, wherein R is a methyl group.

3. The compound of claim 1, wherein R is an ethyl group.

4. The compound of claim 1, wherein $R^1$ represents a hydrogen atom.

5. The compound of claim 1, wherein $R^1$ represents a methyl group.

6. The compound of claim 1, wherein $R^1$ represents an ethyl group.

7. The compound of claim 1, wherein $R^4$ represents a $C_1$-$C_3$ alkyl group.

8. The compound of claim 1, wherein $R^4$ represents a $C_1$-$C_3$ alkenyl group.

9. The compound of claim 1, wherein $R^4$ represents a $C_1$-$C_3$ acyl group.

10. The compound of claim 1, wherein $R^4$ represents a $C_3$-$C_8$ silyl group.

* * * * *